United States Patent [19]
Ligler et al.

[11] Patent Number: 5,496,700
[45] Date of Patent: Mar. 5, 1996

[54] OPTICAL IMMUNOASSAY FOR MICROBIAL ANALYTES USING NON-SPECIFIC DYES

[75] Inventors: Frances S. Ligler, Potomac; Lisa C. Shriver-Lake, Monrovia; Dayaweera C. Wijesuriya, College Park, all of Md.

[73] Assignee: United States of America as represented by The Secretary of the Navy, Washington, D.C.

[21] Appl. No.: 102,933

[22] Filed: Aug. 6, 1993

[51] Int. Cl.$^6$ ............ G01N 33/53; G01N 33/569; C12Q 1/68; C12Q 1/70
[52] U.S. Cl. ............ 435/7.1; 435/7.32; 435/7.3; 435/4; 435/6; 435/5; 435/7.2; 435/7.21; 436/501; 436/518
[58] Field of Search ............ 435/6, 5, 7.2, 7.21, 435/7.22, 7.32, 4, 7.1, 7.3; 436/501, 578, 579, 528, 800, 824

[56] References Cited

U.S. PATENT DOCUMENTS

| | | | |
|---|---|---|---|
| 4,447,546 | 5/1984 | Hirschfield | 436/527 |
| 4,591,570 | 5/1986 | Chang | 436/518 |
| 5,061,857 | 10/1991 | Thompson et al. | 250/458.1 |
| 5,077,210 | 12/1991 | Ligler et al. | 435/176 |

OTHER PUBLICATIONS

Luk et al (1991) "Rapid and Sensitive Detection . . . " J. Immuno. Meth. 137:1–8.
Canning et al (1983) "Identification of bovine . . . " (Abstract Only) Am J Vet Res 44(2):297–300.
D. J. Kemp, D. B. Smith, S. J. Foote, N. Samaras and M. G. Peterson, *Colorimetric detection of specific DNA segments amplified by polymerase chain reactions*, Proc. Natl. Acad. Sci. USA, Medical Sciences, vol. 86, pp. 2423–2427, (Apr. 1989).
P. K. Sorger, G. Ammerer and D. Shore, Identification and Purification of Sequence-Specific DNA-Binding Proteins, in Protein Function: A Practical Approach, pp. 199–223, (T. E. Creignton, Ed.; (1990).
J. J. Devlin et al., *Random Peptide Libraries:A Source of Specific Protein Binding Molecules*, Science, vol. 24, pp. 404–405 (1990).
American Type Culture Collection, Catalogue of Bacteria and Phages, Seventeenth edition, Gherna and Pienta, Eds., (Rockville, Md., 1989).
American Type Culture Collection, Catalogue of Viruses, Animal & Plant, Rickettsiae and Chlamydiae, Seventeenth edition, Gherna and Pienta, Eds., (Rockville, Md., 1989).
M. J. Pelczar, Jr. and R. D. Reid, Microbiology, McGraw-Hill Book Company, New York (1972).
G. L. Humason, Animal Tissue Techniques, 4th Ed., W. H. Freeman and Company, San Francisco (1979).
Sets 4, 18, 29, 31, 33, 34, 35 and 36, Molecular Probes' Handbook of Fluorescent Probes and Research Chemicals, 5th Edition, Molecular Probes Inc., Eugene, Or., pp. 20–22, 100–105, 203–210, 221–242, 249–254, 260–270, (P. R. Haugland, Editor, 1992).
Shriver–Lake, Anderson, Golden and Ligler, *The Effect of Tapering the Optical Fiber on Evanescent Wave Measurements;* Analytical Letters, 25(7), 1183–1199 (1992).
G. P. Anderson, J. P. Golden and F. S. Ligler, *Fiber Optic Biosensor:Combination Tapered Fibers Designed for Improved Signal Acquisition*, Biosensors & Bioelectronics 8, pp. to (1993).
Golden J. P., L. C. Shriver–Lake, G. P. Anderson, R. B. Thompson, F. S. Ligler, *Fluorometer and Tapered Fiber Optic Probes for Sensing in the Evanescent Wave*, Optical Engineering, 31, 1458–1462 (1992).
S. K. Bhatia, S. K., L. C. Shriver–Lake, K. J. Prior, J. H. Georger, J. M. Calvert, R. Bredehorst and F. S. Ligler, *Use of Thiol–Terminal Silanes and Heterobifunctional Crosslinkers for Immobilization of Antibodies on Silica Surfaces*, Anal. Biochem., 178, 408–413, (1989).
G. P. Anderson, L. C. Shriver–Lake, J. P. Golden, F. S. Ligler, *Fiber Optic–Based Biosensor: Signal Enhancement in a Production Model*, SPIE Journal, 1648, 39–43 (1992).
Edward Gurr, Synthetic Dyes in Biology, Medicine and Chemistry, Academic Press, (London & New York, 1971).

*Primary Examiner*—Toni R. Scheiner
*Attorney, Agent, or Firm*—Thomas E. McDonnell; Ajay Pathak

[57] ABSTRACT

The presently disclosed invention relates to a method of rapid detection and identification of microorganisms including bacteria, viruses, rickettsiae and fungi. The method involves staining all microorganisms or fragments thereof in a sample. The stained sample is introduced onto an optical waveguide coated with a capture molecule specific for the microorganism of interest, and the bound microorganism or fragment thereof is then optically detected. For example, detection of *B. anthracis* and Salmonella was achieved in times of approximately one minute. The sensitivity of this method is on the order of about 3 cells/µl.

5 Claims, 6 Drawing Sheets

OPTICAL IMMUNOASSAY FOR MICROBIAL ANALYTES USING NON-SPECIFIC DYES

BACKGROUND OF THE INVENTION

1. Field of the Invention

The present invention relates to a method for detecting the suspected presence of a microbial analyte within a sample. More specifically, the present invention relates to an optical detection method using non-specific dyes for detecting the suspected presence of microbial analytes, for example, bacteria, viruses, fungi, rickettsiae and fragments of these microbial analytes among others.

2. Description of the Related Art

There is a requirement for rapid methods of detection and identification of microbial analytes, for example, microorganisms, bacteria, viruses, rickettsiae, fungi and their fragments not only for medical diagnosis, but also for agriculture, food processing, bioprocessing and water purification. Current methods include cell culture, microscopy, immunoassay and nucleic acid probes. Assay times vary from days to minutes. Only culture and polymerase chain reaction (PCR) based tests are very sensitive. Culture and microscopy depend on the isolation of the intact microorganisms from the milieu to be tested, and, for culture, the cells must be viable. Tests based on genetic methods, including polymerase chain reaction, require intact deoxyribonucleic acid (DNA) or ribonucleic acid (RNA). The tradeoffs inherent in these various methods are summarized below.

and M. G. Peterson in *Colorimetric detection of specific DNA segments amplified by polymerase chain reactions*, PROC. NATL. ACAD. SCI. USA, MEDICAL SCIENCES, Vol. 86, pp. 2423–2427, (April 1989) and by P. K. Sorger, G. Ammerer and D. Shore in chapter eight (8) titled IDENTIFICATION AND PURIFICATION OF SEQUENCE-SPECIFIC DNA-BINDING PROTEINS, in PROTEIN FUNCTION: A PRACTICAL APPROACH, pp. 199–223, (T. E. Creignton, Ed.; (1990), each reference incorporated herein by reference in its entirety and for all purposes. Other binding molecules include receptors and synthetic peptides listed in *Random Peptide Libraries: A Source of Specific Protein Binding Molecules* by J. J. Devlin et al. published in SCIENCE, Vol. 24, pp. 404–405 (1990), incorporated herein in its entirety by reference and for all purposes.

The use of optical waveguide fibers as a special class of waveguides for immunoassays has been known. For example, U.S. Pat. No. 4,447,546 (Hirschfield, 1984) discloses the use of optical fibers as waveguides which capture and conduct fluorescence radiation emitted by molecules near their surface. U.S. Pat. No. 5,061,857 (Thompson et al., 1991) discloses an optical waveguide-binding sensor having improved sensitivity for use with fluorescence assays.

In the aforementioned patents, the analyte is specifically labeled such that the antibody-analyte complex formed on the optical fiber waveguide is detected due to the fluorescence signal excited and guided toward a fluorimeter using the evanescent wave portion of the optical fiber.

Among the various detection methods, for example, cell culture, microscopy, immunoassay and PCR anasysis, none

|  | Time | Sensitivity | Specificity | Technical Complexity |
|---|---|---|---|---|
| Cell culture | 1–3 days | high, if microorganism viable | moderate | simple for bacteria; difficult for viruses |
| Microscopy |  |  |  |  |
| conventional stain | hours | low | moderate | moderate |
| selective stain | 5 minutes | low | moderate | simple |
| immunofluorescence | hours | low | high | moderate |
| immunoassay |  |  |  |  |
| ELISA (enzyme linked immunosorbent assay | 3–4 hours | moderate | good | moderate |
| dip-stick | 20–30 minutes | moderate | good | simple |
| latex turbidity | 15 minutes | moderate | good | simple |
| gene probe dot blot | 1 hour | moderate | excellent | moderate |
| PCR (polymerase chain reaction) | 2 hours | high | excellent | complex |

In the immunoassay and immunofluorescence stains previously described, a complex is formed between the antibody, the analyte recognized (from or on the microorganism) and a label or signal generator (i.e. enzyme) that can be measured. The measurement may represent the formation of such a complex, as in sandwich immunoassays, or the lack of formation of such complexes, as in most competitive immunoassays. In a sandwich immunoassay, the label or signal generator is attached to an antibody. There is no direct attachment of the label to the analyte. The binding of the label or signal generator to the analyte is via the antibody.

In a competitive assay, the label or signal generator is bound to an antigen similar to the analyte. As the analyte competes with the labeled antigen for binding to the antibody, the amount of signal changes. In this case also, the label never directly attaches to the analyte.

Other binding molecules besides antibodies have been demonstrated to be useful in sandwich and competitive assays. Such binding molecules include, but are not limited to, lectins, deoxyribonucleic acid (DNA) binding proteins listed by D. J. Kemp, D. B. Smith, S. J. Foote, N. Samaras offer all the advantages of high sensitivity, short assay times (approximately under 5 minutes) and low technical complexity. Furthermore, all of the above patents disclose the use of dyes attached to specific binding molecules (i.e. antibodies or antigens). Assays using dyes bound to specific binding elements may require an incubation time, may be very limited in the amount of the dye that is actually associated with the analyte, and may introduce multi-step procedures into the assay.

In addition to immobilization of antibodies for assay purposes, antibodies on solid supports have been used to bind intact cells and remove them from complex mixtures containing other cell types. Most commonly used forms of this approach are affinity chromatography and panning. In both cases, the sample, containing mixtures of cells, is incubated with the antibody-coated solid support and then the support is gently but thoroughly washed. The bound cells are eluted and subsequently may be subjected to a variety of characterization or experimental procedures. Affinity chromatography and panning techniques are used for isolation purposes rather than for detection of microorganisms or microbial analytes. Such techniques are relatively time consuming, inefficient in terms of cell recovery, and require technical training.

SUMMARY OF THE INVENTION

It is therefore an object of the present invention to detect the presence of a microbial analyte in a rapid, simple manner.

It is another object of the present invention to detect the presence of a microbial analyte without the use of dyes attached to specific binding molecules.

It is yet another object of the present invention to incorporate a large number of dye molecules in each complex of the dye, the microbial analyte and the capture molecules.

It is a further object of the present invention to specifically immobilize and detect a stained microbial analyte.

It is yet a further object of the present invention to detect low concentrations of the microbial analyte, for example, as low as 3000 cells/ml.

It is an even further object of the present invention to detect the microbial analyte in environmental or clinical samples.

These and other objects are accomplished by the use of non-specific dyes which stain all material from, for example, a biological source. The sample, suspected of containing the microbial analyte, is mixed with the dye and then exposed to a solid support material which has attached to it capture molecules specific for the suspected microbial analyte. If the suspected microbial analyte is present, then the non-specifically stained microbial analyte binds to the analyte-specific capture molecules. The solid support is constructed so that it can be integrated into an optical readout system for direct measurement of the amount of stained microbial analyte bound by the analyte-specific capture molecules.

BRIEF DESCRIPTION OF THE DRAWINGS

A more complete appreciation of the present invention and several of the accompanying advantages thereof will be readily obtained by reference to the following detailed description when considered in conjunction with the accompanying drawings, wherein.

Figure 1:
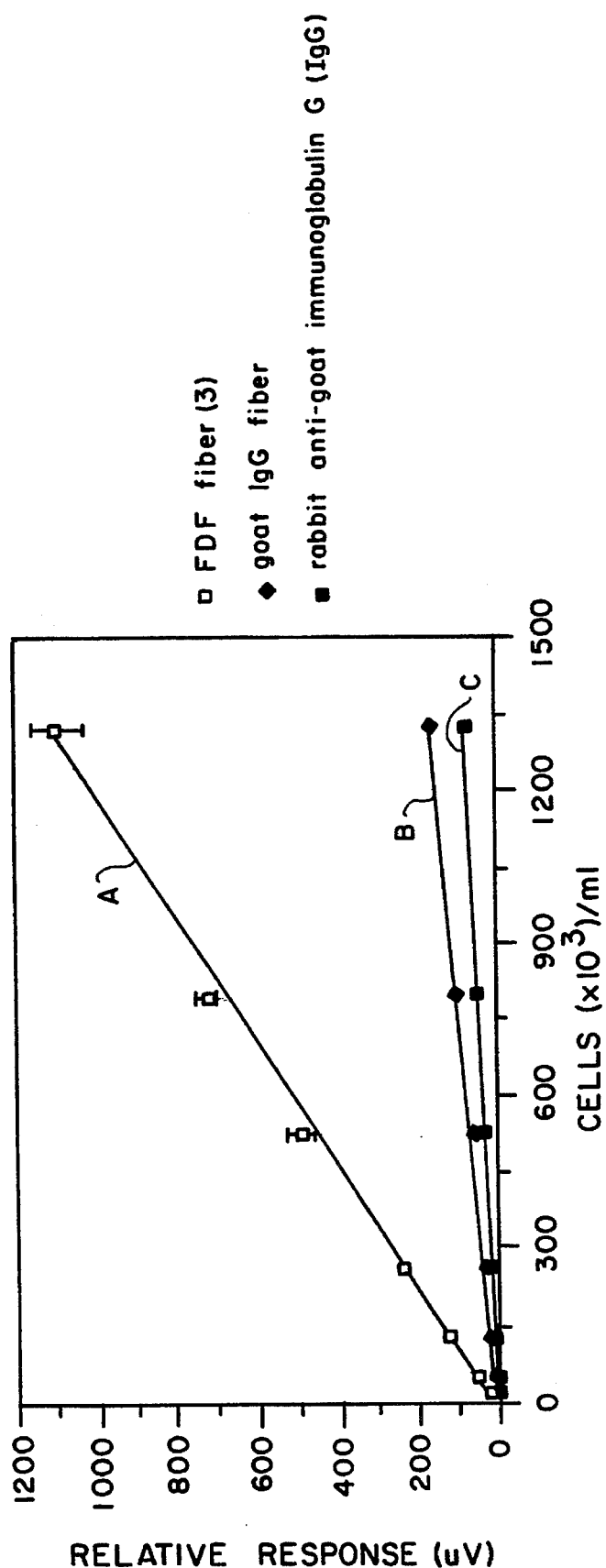
FIG. 1 is a plot of microbial analyte (*B. anthracis*) concentration versus optical signal, measured in microvolts (μV), produced by a complex, attached to an optical fiber, of Nile red, *B. anthracis* and a capture molecule, an antibody, referred to in EXAMPLE 2. Curve A was produced by the complex of Nile red, *B. anthracis* and FDF-1B9, an antibody specific for *B. anthracis*. Curve B was produced by the complex of Nile red and *B. anthracis* in the presence of an optical fiber coated with goat immunoglobulin G (goat IgG). Curve C was produced by the complex of Nile red and *B. anthracis* in the presence of an optical fiber coated with rabbit anti-goat immunoglobulin G (rabbit anti-goat IgG).

FIG. 2 is schematic representation of a stained microbial analyte 30 attached to a capture molecule 20 attached to optical fiber 10 referred to in EXAMPLE 2.

FIG. 3 is a plot similar to that in FIG. 1. However, the microbial analyte (*B. anthracis*) concentration has been decreased. Curve A was produced by the complex of Nile red, *B. anthracis* and FDF-1B9, an antibody specific for *B. anthracis*. Curve B was produced by the complex of Nile red and *B. anthracis* in the presence of an optical fiber coated with mouse immunoglobulin G (goat IgG). Curve C was produced by the complex of Nile red and *B. anthracis* in the presence of an optical fiber coated with rabbit anti-goat immunoglobulin G (rabbit anti-goat IgG).

FIG. 4 is a plot of microbial analyte concentration versus optical signal, measured in microvolts (μV), produced by a complex, attached to an optical fiber, of Nile red, microbial analyte and a capture molecule, an antibody, referred to in EXAMPLE 5. Curve A was produced by the complex of Nile red, B. anthracis and FDF-1B9. Curve B was produced by the complex of Nile red and *B. subtilis* in the presence of an optical fiber coated with FDF-1B9.

FIG. 5 is a bar graph representation of trial number (no. of uses) versus optical signal, measured in μV, over background produced by a complex, attached to an optical fiber, of Nile red, *B. anthracis* and FDF-1B9 referred to in EXAMPLE 6. Note that between trials, the optical fiber was washed as indicated in EXAMPLE 6.

FIG. 6 is a plot of microbial analyte concentration (*B. anthracis* in river water) versus optical signal, measured in μV, produced by a complex, attached to an optical fiber, of Nile red, a microbial analyte and a capture molecule, an antibody, referred to in EXAMPLE 7. Curve A is produced by a complex of Nile red, *B. anthracis* and FDF-1B9. Curve B is produced by a complex of Nile red and *B. anthracis* in the presence of an optical fiber coated with mouse immunoglobulin G (mouse IgG).

FIG. 7 is a plot of microbial analyte concentration (*B. anthracis* in serum) versus optical signal, measured in μV, produced by a complex, attached to an optical fiber, of Nile red, a microbial analyte and a capture molecule, an antibody, referred to in EXAMPLE 7. Curve A is produced by a complex of Nile red, *B. anthracis* and FDF-1B9. Curve B is produced by a complex of Nile red and *B. anthracis* in the presence of an optical fiber coated with mouse immunoglobulin G (mouse IgG).

FIG. 8 is a plot of time versus optical signal measured in μV produced by a complex, attached to an optical fiber, of ethidium bromide, Salmonella, and a capture molecule, an antibody specific for Salmonella, referred to in EXAMPLE 10. Curve A is produced by a complex of ethidium bromide, Salmonella and an antibody specific for Salmonella. Curve B is produced by a complex of ethidium bromide and Salmonella in the presence of an optical fiber coated with non-specific immunoglobulin G (IgG).

FIG. 9 is a plot of time versus optical signal, measured in μV, produced by a complex, attached to an optical fiber, of Nile red, *B. anthracis* and FDF-1B9 referred to in EXAMPLE 3.

DETAILED DESCRIPTION OF THE INVENTION

The following detailed description of the preferred embodiment is provided to aid those skilled in the art in practicing the present invention. However, the following detailed description of the preferred embodiment should not be construed to unduly limit the present invention. Variations and modifications in the embodiments discussed may be made by those of ordinary skill in the art without departing from the scope of the present inventive discovery.

For purposes of consistent usage of terminology, a microbial analyte is defined as a microorganism or fragments thereof which are uniquely associated with a specific microorganism or class of microorganisms. Thus, a microbial analyte includes, for example, the following: a bacteria or fragments thereof, a virus or fragment thereof, a fungi or fragments thereof, rickettsiae or fragments thereof among others.

With respect to microbial analytes that are bacteria or fragments thereof, fungi or fragments thereof, viruses or fragments thereof, rickettsiae or fragments thereof, they include, but are not limited to, the following:

*Mitoplasma capsulatum, Cryptococcus neoformans, Blastomyces dermatitidis, Paracoccidioides brasilenensis, Coccidioides immitis, Corynebactedum diphthedae, Corynebactedum heamolyticum, Corynebacterium pseudodiphtheriticum, Corynebacterium pseudotuberculosis, Corynebactedum ulcerans, Corynebactedum xerosis, Bacillus anthracis, Bacillus thurengensus, Pneumocistis pneumoniae, Treponema pallidum, Treponema pertenue, Treponema carateum, Leptospira interrogans, Borrelia recurrentis, Borrelia burdorfed, Legionella pneumophila, Legionella micdadei, Legionella bozemanii, Legionella dumoffii, Legionella gormanii, Legionella longbeacheae, Legionella jordanis, Rickettsiae rickettsii, Rickettsiae prowazekii, Rickettsiae moosed, Rickettsiae tsutsugamushi, Rickettsiae akari, Coxiella burnetii, Vibrio cholerae, Vibrio parahaemolyticus, Vibrio alginolyticus, Vibrio vulnifcus, Vibrio hollisae, Vibrio mimicus, Vibrio fluvialis, Vibrio damsela, Vibrio metschnikovii, Aeromonas hydrphila, Plesiomonas shigelloides, Salmonella typhi, Salmonella entedditis, Arizona hinshawii, Edwardsiella tarda, Shigella dysentedae, Shigella flexneri, Shigella boydii, Shigella sonnei, Yersinia enterocolitica, Yersinia pseudotuberculosis, Yersinia pestis, Escherichia coli, Neisseria meningitidis, Nesseria gonorrhoeae, Hemophilus influenzae, Bordetella pertussis, Trypanosoma cruzi, Plasmodium vivax, Leishmania spp., Histoplasma capsulatum, Schistosoma mansoni, Trichinella spiralis, Streptococcus pneumoniae, Streptococcus pyogenes, Staphylococcus epidermidis, Staphylococcus albus, Equine encephalitis* virus, Rabies virus, Jungle yellow fever virus, Tomato bushy stunt virus, Tobacco mosaic virus, *Alfalfa mosaic* virus, rotaviruses, parvoviruses, adenoviruses, enteroviruses, Herpes simplex virus, Human immunodeficiency virus (Type I, II, III and IV), *Candida albicans, Myxomyceteae plasmodiophora, Myxomyceteae spongospora, Phycomyceteae aphanomyces, Ascomyceteae ceratocystis, Ascomyceteae mycosphaerella, Deuteromyceteae alternada, Basidiomyceteae ustilago* and *Trichomonas vaginalis* among others too numerous to list here. Also, additional microbial analytes are listed in American Type Culture Collection, CATALOGUE OF BACTERIA AND PIIAGES, Seventeenth edition, Gherna and Pienta, Eds., (Rockville, Md., 1989) and American Type Culture Collection, CATALOGUE OF VIRUSES, ANIMAL & PLANT, RICKETFSIAE AND CHLAMYDIAE, Seventeenth edition, Gherna and Pienta, Eds., (Rockville, Md., 1989), each reference incorporated herein by reference in its entirety and for all purposes. Other microbial analytes are listed in M. J. Pelczar, Jr. and R. D. Reid, MICROBIOLOGY, McGraw-Hill Book Company, New York (1972), incorporated herein by reference in its entirety and for all purposes.

To a given sample of material suspected of containing a microbial analyte of interest (for example, a bacteria or fragments thereof, viruses or fragments thereof, fungi or fragments thereof and rickettsiae or fragments thereof) a non-specific dye which stains biological elements is added. A non-specific dye is a dye which specifically labels neither the microbial analyte, a binding element specific to the microbial analyte, nor an analog of the analyte that competes with the analyte for binding to a binding element specific to the analyte. A biological element of a microbial analyte includes, but is not limited to, membranes, cell walls, DNA, RNA, cytoskeletal structures, mitochondria and fragments thereof. In the preferred embodiment of the invention, the dye is fluorescent. Dyes which label, for example, metals, carbohydrates, nucleic acids, lipids or proteins can be used. Several of these dyes are given by G. L. Itumason in ANIMAL TISSUE TECHNIQUES, 4th Ed. (1979), incorporated herein by reference in its entirety and for all purposes. Another preference is for dyes that have low fluorescence in aqueous media, but fluoresce when intercalated into microorganisms (including the microbial analyte of interest) and their fragments. Dyes that fluoresce at wavelengths where the unstained sample exhibits relatively low levels of fluorescence are also preferred. Suitable nonspecific dyes may be selected from those used to stain lipids or DNA or proteins or carbohydrates. Among such dyes are the nucleic acid stains, for example, ethidium bromide, ethidium diazide, propidium iodide and others listed in Set 31: Nucleic Acid Stains in MOLECULAR PROBES' HANDBOOK OF FLUORESCENT PROBES AND RESEARCH CHEMICALS, 5TH EDITION, MOLECULAR PROBES INC., EUGENE, OREGON (P. R. HAUGLAND, EDITOR, 1992). Other suitable dyes include isothiocyanates (Set 4), probes for following cndocytosis (Set 18), probes for cytoskeletal components and metabolic indicators (Set 29), labeled phospoholipids (Set 33), artionic membrane probes (Set 34), cationic probes (Set 35) and neutral membrane probes (Set 36). Id. The list of dyes given in Sets 4, 18, 29, 31, 33, 34, 35 and 36 listed in MOLECULAR PROBES' HANDBOOK OF FLUORESCENT PROBES AND RESEARCH CHEMICALS, 5TH EDITION, MOLECULAR PROBES INC., EUGENE, OREGON (P. R. HAUGLAND, EDITOR, 1992) are incorporated herein by reference in their entirities and for all purposes.

Among the nonionic dyes (neutral probes), there are four classes of dyes including acidic, basic, neutral and amphoteric dyes. Among the cationic dyes (cationic probes), there are two classes of dyes including wholly basic dyes and basic dyes having acidic side chains. Among the anionic dyes (anionic probes), there are three subgroups of dyes including wholly acidic dyes, weakly amphoteric dyes, and moderately or strongly amphoteric dyes.

The anionic wholly acidic dyes further include six classes of dyes including carboxylated dyes without hydroxyl groups, carboxylated dyes with hydroxyl groups, sulphonated dyes without hydroxyl groups, sulphonated dyes with hydroxyl groups, sulphonated dyes with carboxyl groups and hydroxyl groups and dyes with hydroxyl groups as their only colligators. The anionic weakly amphoteric dyes further include two classes of dyes including those dyes with hydroxyl groups and those dyes without hydroxyl groups. The anionic moderately or strongly amphoteric dyes further include three classes of dyes including those dyes without hydroxyl groups, those dyes with hydroxyl groups and those dyes with hydroxyl groups as their only acidic colligators. Numerous examples of these nonionic cationic and anionic dyes are given by Edward Gurr and are suitable as nonspecific dyes for use in conjunction with the present inventive process published in SYNTHETIC DYES IN BIOLOGY, MEDICINE AND CHEMISTRY, Academic Press, (London & New York, 1971), incorporated herein by reference in its entirety and for all purposes.

Once microbiological material within a sample suspected of containing the microbial analyte is stained using a non-specific dye, the stained sample is introduced over a solid support coated with a capture molecule specific for the microbial analyte of interest. The capture molecule can be adsorbed or covalently bound to the solid support. One procedure for immobilizing capture molecules onto a solid support material is given in U.S. Pat. No. 5,077,210 of Ligler et al., incorporated herein by reference in its entirety. Of course, other immobilization procedures may be used in order to optimize these procedures to maintain the binding function of the capture molecule. the method used for immobilization is not critical to the present invention. Capture molecules include but are not limited to antibodies, lectins, cell receptors, DNA binding proteins or specifically engineered peptides referenced in *Random Peptide Libraries: A Source of Specific Protein Binding Molecules* by J. J. Devlin et al. published in SCIENCE, Vol. 24, pp. 404–405 (1990), incorporated herein by reference in its entirety and for all purposes. Antibodies may be preferred simply because of their specificity, availability and stability following immobilization.

If the target analyte is present, the introduction of the stained sample to the solid support coated with a capture molecule (for example, an antibody specific for the microbial analyte) results in the formation of a complex including the dye, the microbial analyte and the capture molecule. The presence of a suspected microbial analyte is confirmed by detection of the optical signal of the dye-microbial analyte-capture molecule complex.

A number of materials are suitable solid support materials upon which the capture molecules can be immobilized. Such solid support materials include silicon, glass, fused silica, plastics, paper and polymers, such as hydrogels, nitrocellulose and polystyrene. These solid support materials can have a variety of shapes including slides, coverslips, tubes, beads, membranes, microtiter plates and chromatographic strips among others.

After allowing for the possible formation of a complex including a dye, a microbial analyte, and a capture molecule, unbound microorganisms or fragments thereof may or may not require washing away depending on the optical readout method. If the solid support is, for example, a microscope slide, then after exposure of the stained microbial analyte to the analyte-specific capture molecules, the slide is washed. Only the immobilized complex of the dye, the microbial analyte and the capture molecule remains on the slide after washing and can be visually or photometrically detected, if present. If the solid support is an optical fiber, then excitation of the dye-microbial analyte-capture molecule complex can be carried out using the light in the evanescent wave portion (approximately within 100 nm of the fiber core) of the optical fiber. Antibody- based sensing using evanescent wave detection has been carried out by Shriver-Lake, Anderson, Golden and Ligler as described in *The Effect of Tapering the Optical Fiber on Evanescent Wave Measurements* and published in ANALYTICAL LETTERS, 25(7), 1183–1199 (1992), incorporated herein by reference in its entirety and for all purposes. In addition, fiber optic probes have been carefully fashioned to achieve both optimal excitation of the bound fluorophore and capture of its subsequent emission. See L. C. Shriver-Lake, G. P. Anderson, G. P. Golden and F. S. Ligler, *The Effect of Tapering the Optical Fiber on Evanescent Wave Measurements*, ANAL. LETT. 25 (7): 1183–1199 (1992), incorporated herein by reference in its entirety and for all purposes; See G. P. Anderson, J. P. Golden and F. S. Ligler, *Fiber Optic Biosensor: Combination Tapered Fibers Designed for Improved Signal Acquisition*, BIOSENSORS & BIOELECTRONICS 8 (1991), incorporated herein by reference in its entirety and for all purposes.

Dyes can be used which generate, for example, visible, fluorescence, luminescence, colorimetric, infrared (IR) and ultraviolet (UV) signals. The methods of measuring the dye-microbial analyte-capture molecule complexes include, for example, spectroscopy, microscopy, visual detection, electron spin resonance, phosphorescence and optical waveguide detection.

The following examples outline preferred embodiments of the present invention.

EXAMPLE 1

Choice of Stain for Assay

To select a dye appropriate for use with the microbial analyte of interest and the optical readout system selected by the user, it must be determined that the dye does stain the microbial analyte of interest and does not produce a positive signal (i.e. no false positives) in the absence of the microbial analyte. In preparation for the detection of *B. anthracis* using fluorescence microscopy, $10^8$ cells/ml were stained with varying concentrations of different dyes. Nucleic acid dyes (ethidium bromide, acridine orange), a lipid soluble dye (Nile red) and a cationic dye (D-384, a styryl dye) were tested.

The stock solution (50 µl, $10^8$ cells/ml, *B. anthracis*) of encapsulated vegetative cell (double irradiated and formaldehyde fixed) was incubated in 250 µl of dye for about 20 minutes. Microscope slides were spotted with a few microliters of each cell preparation and examined using a fluorescence microscope for stained bacilli. The table below summarizes the results of the fluorescence microscopic studies of *B. anthracis* staining. Brightness of the bacteria over background signal was estimated visually and qualitatively graded from "–" (no fluorescence) to "++++" (staining equal to that seen with Nile red at $2.2 \times 10^{-5}$M).

| STAINING DYE | MOLAR CONCENTRATION | STAINING INTENSITY |
|---|---|---|
| Propidium iodide | $8.5 \times 10^{-4}$ | ++++ |
| Propidium iodide | $8.5 \times 10^{-6}$ | ++++ |
| Propidium iodide | $8.5 \times 10^{-7}$ | +++ |
| Propidium iodide | $8.5 \times 10^{-8}$ | + |
| Ethidium bromide | $1.7 \times 10^{-3}$ | ++++ |
| Ethidium bromide | $1.7 \times 10^{-5}$ | ++++ |
| Ethidium bromide | $1.7 \times 10^{-6}$ | +++ |
| Ethidium bromide | $1.7 \times 10^{-7}$ | + |
| Acridine orange | $1.2 \times 10^{-3}$ | ++++ |
| Acridine orange | $1.2 \times 10^{-5}$ | – |
| Acridine orange | $1.2 \times 10^{-6}$ | – |
| Acridine orange | $1.2 \times 10^{-7}$ | – |
| Nile red | $2.2 \times 10^{-5}$ | ++++ |
| Nile red | $2.2 \times 10^{-6}$ | ++++ |
| Nile red | $2.2 \times 10^{-7}$ | +++ |
| Nile red | $2.2 \times 10^{-8}$ | + |
| D-384 | $3.27 \times 10^{-5}$ | ++++ |
| D-384 | $3.27 \times 10^{-7}$ | ++ |
| D-384 | $3.27 \times 10^{-8}$ | – |
| D-384 | $3.27 \times 10^{-9}$ | – |

EXAMPLE 2

Detection of Nile Red-Stained Microbial Analytes

The mouse monoclonal antibody, FDF-1B9, specific for capsular material of *B. anthracis* vegetative cells (obtained from Dr. John Ezzell, US Army Institute of Infectious Diseases, Ft. Derrick, Md.) was received as ascites. Immunoglobulin G (IgG) fractions were prepared using protein G-agarose. Protein G affinity columns were equilibrated with 0.01M phosphate buffered saline, pH 7.0. Ascites fluid, diluted 1:2 was applied directly to the column and washed with phosphate buffered saline (PBS) at pH 7.4. Antibodies were eluted from the column with 0.05M ammonium acetate, pH 3.0 and pooled fractions dialyzed against PBS. Protein concentrations were determined using adsorption at 280 nanometers.

Cladding from the distal 12 cm of the fiber (fused silica, 200 microns in diameter) was stripped away using a razor blade and the exposed core was tapered by slow immersion into hydrofluoric acid (33%). After tapering, the decladded portion was acid cleaned to generate the surface hydroxyl groups required for protein immobilization by crosslinking. The fibers were immersed in a 2% solution of 3-mercaptopropyltrimethoxy silane in toluene for 30 minutes under an inert atmosphere, then rinsed in toluene. Next, the silanized fibers were immersed in a 2 mM solution of the heterobifunctional crosslinked, gamma-maleimidylbutyryl succinimide, for 1 hour and rinsed with phosphate buffered saline pH 7.4. Finally, the fibers were incubated for 1 hour in a solution containing 0.05 mg/ml specific antibody (FDF-1B9) or goat IgG (control) in PBS and rinsed with PBS several times. The IgG-coated fibers were stored in PBS containing 0.02% sodium azide when not in use. Details of the tapering and immobilization procedures can be found in Golden J. P., L. C. Shriver-Lake, G. P. Anderson, R. B. Thompson, F. S. Ligler, *Fluorometer and Tapered Fiber Optic Probes for Sensing in the Evanescent Wave*, OPTICAL ENGINEERING, 31, 1458–1462 (1992), incorporated herein by reference in its entirety and for all purposes, and S. K. Bhatia, S. K., L. C. Shriver-Lake, K. J. Prior, J. H. Georger, J. M. Calvert, R. Bredehorst and F. S. Ligler, *Use of Thiol-Terminal Silanes and Heterobifunctional Crosslinkers for Immobilization of Antibodies on Silica Surfaces*, ANAL. BIOCHEM., 178, 408–413, (1989), incorporated herein by reference in its entirety and for all purposes. The latter reference discloses the use of thiol-terminal silanes and heterobifunctional crosslinkers for immobilization of antibodies on silica surfaces.

The fluorimeter portion of the fiber optic biosensor consists of a 50 mW argon-ion laser, an off-axis parabolic mirror and spherical lens. The laser beam (514 nm) passed through the off-axis parabolic mirror, and was focused by the spherical lens onto the proximal end of the fiber. A chopper was placed between the spherical lens and the fiber and interfaced to a lock-in amplifier for phase-sensitive detection. The collected fluorescence signal traveled the reverse path to the parabolic mirror where it was refocused through a bandpass filter (KV550) onto a silicon photodiode which was also connected to the lock-in amplifier. Data was collected using a lap-top computer. A detailed description of this fiber optic fluorimeter can be found in G. P. Anderson, L. C. Shriver-Lake, J. P. Golden, F. S. Ligler, *Fiber Optic-Based Biosensor: Signal Enhancement in a Production Model*, SPIE JOURNAL, 1648, 39–43 (1992), incorporated herein by reference in its entirety and for all purposes.

The antibody-coated region of an optical fiber was mounted in a glass capillary tube using T-connectors at both ends. The distal end of the fiber was blocked with a non-fluorescent glue.

Figure 2:
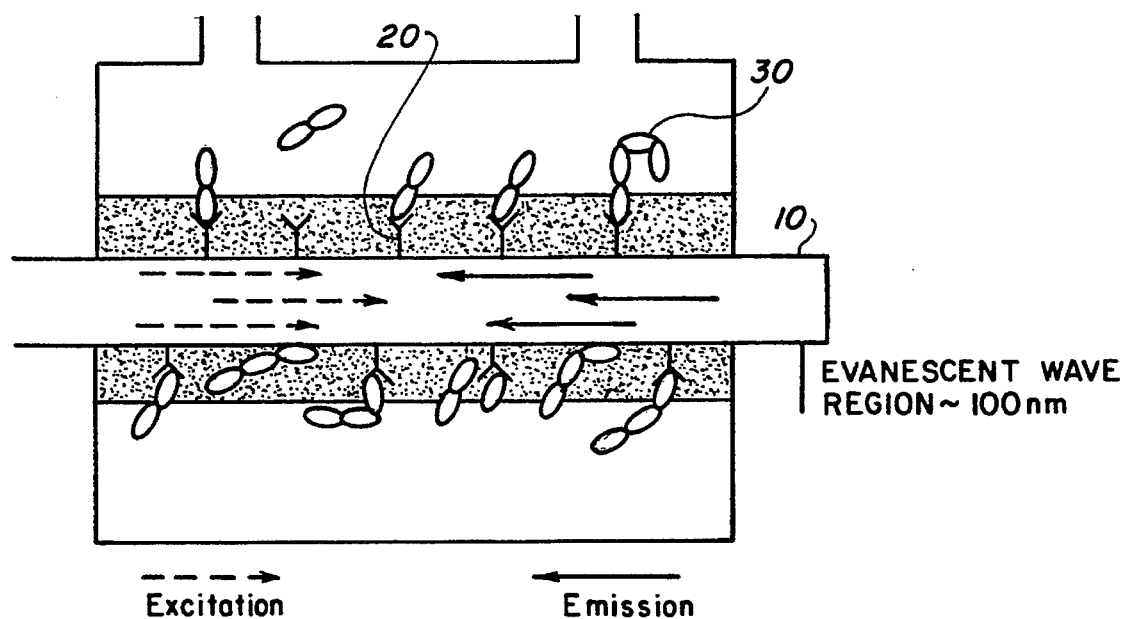

A dose/response curve of demonstrating the capability of the assay to detect Nile red-stained *B. anthracis* (vegetative cells) was obtained as follows: Vegetative cells ($4.4 \times 10^8$ cells) were washed once with 4.0 ml of PBS. Cells were incubated in 4.0 ml of Nile red ($10^{-6}$ Molar) for 15 minutes. After dilution with PBS, the concentration of Nile red-stained cells in the stock suspension was $1.6 \times 10^4$ cells/µl. A series of suspensions of stained cells, ranging in concentration from 26 to 1333 cells/µl, were prepared by dilution of the stock suspension with PBS. Non-specific binding sites on the fiber were blocked with PBS+0.5% gelatin+0.3% Tween 20 (PBSGT) before introducing cell suspensions. Fluorescence signals were recorded when a fiber 10 coated with antibodies 20 was exposed to increasing concentration of stained cells 30 as shown in FIG. 2.

Relative responses of fibers coated with FDF-1B9 (specific IgG antibody, FIG. 1: curve A), goat IgG (control, FIG. 1: curve B) or rabbit anti-goat IgG (control, FIG. 1: curve C) were plotted against concentrations of stained cells as shown. The results indicate a response in direct proportion to the concentration of cells in the suspension. Visual examination of the fiber under a microscope showed that the cells had indeed been immobilized onto the surface of the optical fiber.

EXAMPLE 3

Demonstration of Rapid Assay Time

Figure 9:
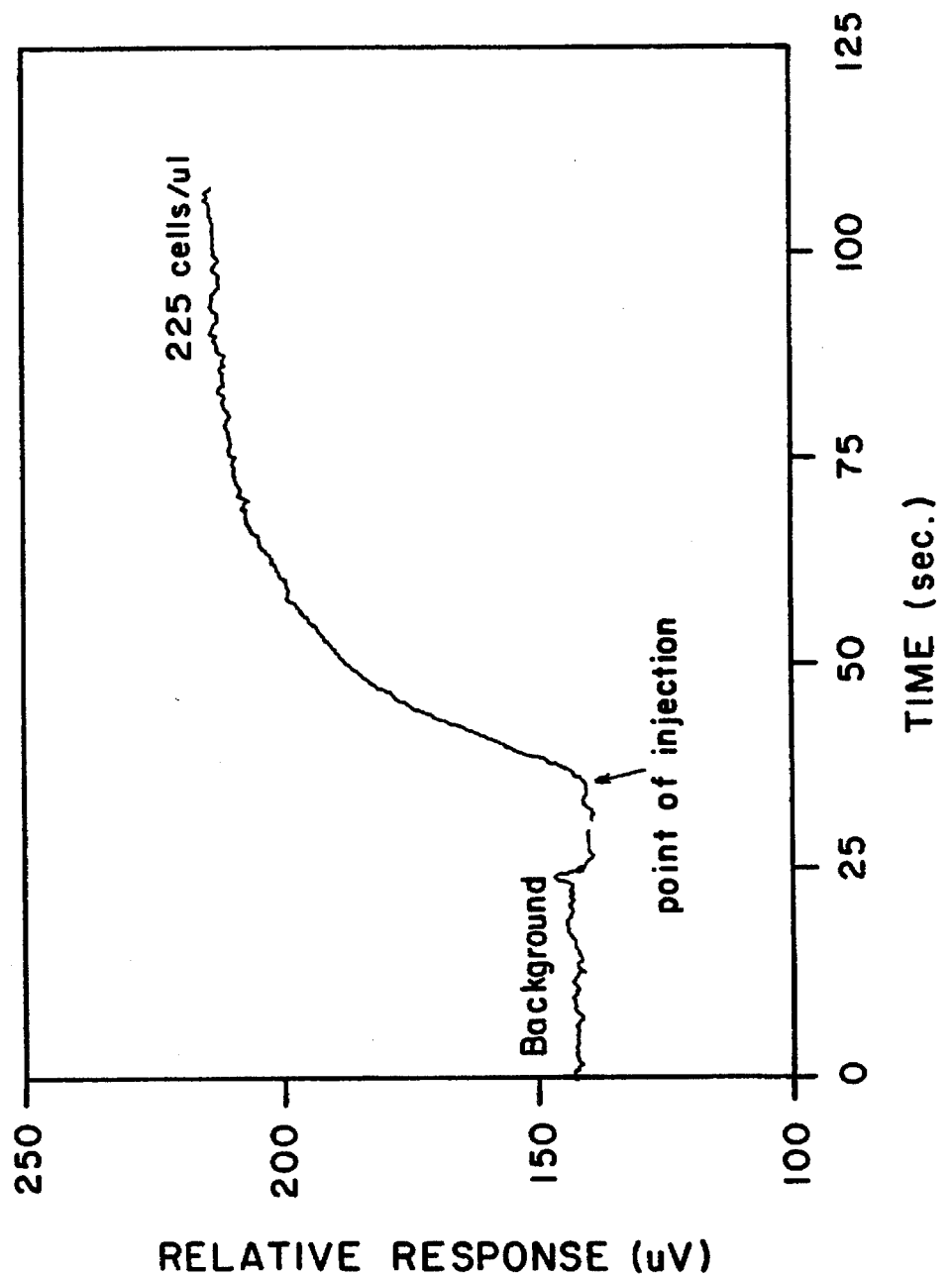

A response/time curve of the assay using Nile red-stained *B. anthracis* cells and the fiber optic biosensor readout system was obtained as follows: A fiber coated with specific antibody FDF-1B9 was exposed to *B. anthracis* cells (225 cells/µl) stained with Nile red as described in EXAMPLE 2. The voltage was monitored for about 3 minutes to record the increase in fluorescence signal with time. As shown in FIG. 9, the t-90 (time required to reach 90% of total response) value calculated from the response/time curve was on the order of 35 seconds.

EXAMPLE 4

Demonstration of Assay Sensitivity

Sensitivity and possible detection limits of the assay were investigated for the FDF-1B9 antibody and *B. anthracis* cells stained using Nile red and using the fiber optic biosensor as the readout system as described in EXAMPLE 2.

Figure 3:
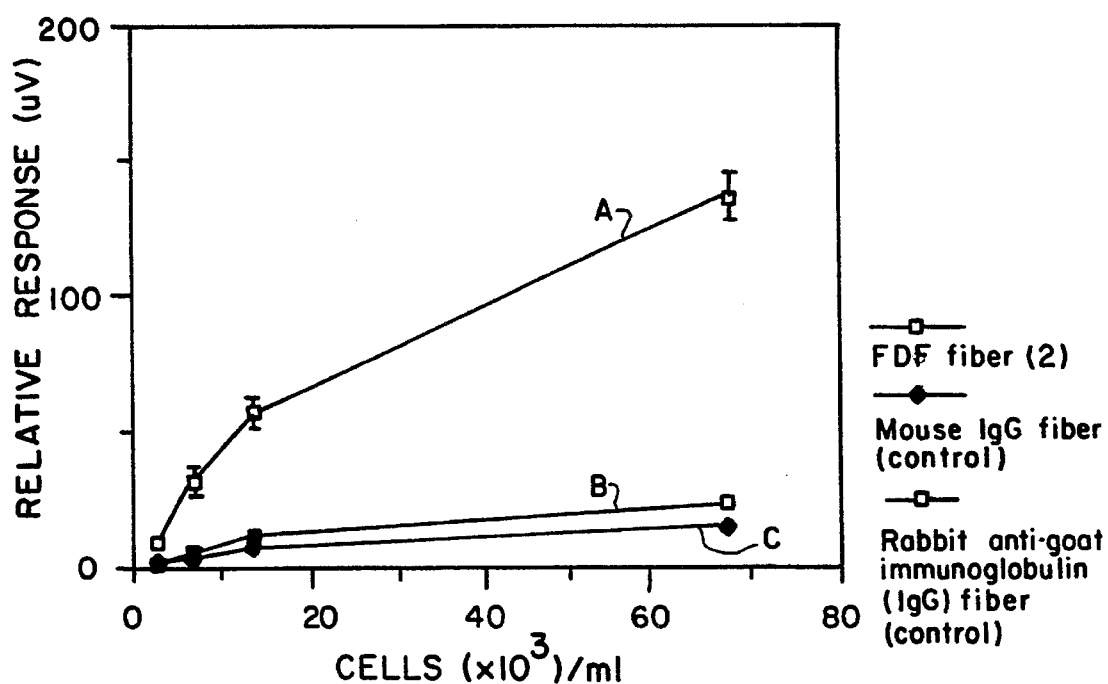

Dose/response curves (FIG. 3) of the assay for stained cells (concentrations ranging from 3 to 50 cells/µl) were obtained as described in EXAMPLE 3. Lowest detection limit of the assay obtained with this particular antibody-cell pair and under these particular conditions was 3 cells/µl or about 1000 cells. The volume of the reaction chamber into which the fiber was inserted was 325 µl. The use of larger volumes or improvements in the biosensor itself might lower the limits of sensitivity even further.

EXAMPLE 5

Demonstration of Assay Selectivity

Selectivity of the assay was evaluated using the FDF-1B9 antibody, *B. anthracis* and a similar bacteria *B. subtilis*, Nile red stain, and the fiber optic biosensor. The assay procedure was performed as in EXAMPLE 2, with respect to the FDF-1B9 antibody coated fiber.

Response of the sensor for Nile red-stained *B. anthracis* (vegetative form, FIG. 4: curve A) and *B. subtilis* (vegetative form, FIG. 4: curve B) were compared as shown. Fibers coated with specific antibodies to *B. anthracis* (FDF-1B9) were exposed to Nile red-stained *B. anthracis* and *B. subtills* cells at increasing concentrations (12–160 cells/µl). Fluorescence signals were plotted against each cell concentration. The specificity of the antibody is maintained under the conditions of the assay.

EXAMPLE 6

Demonstration of Reusability of the Assay Apparatus

Figures 4, 5:
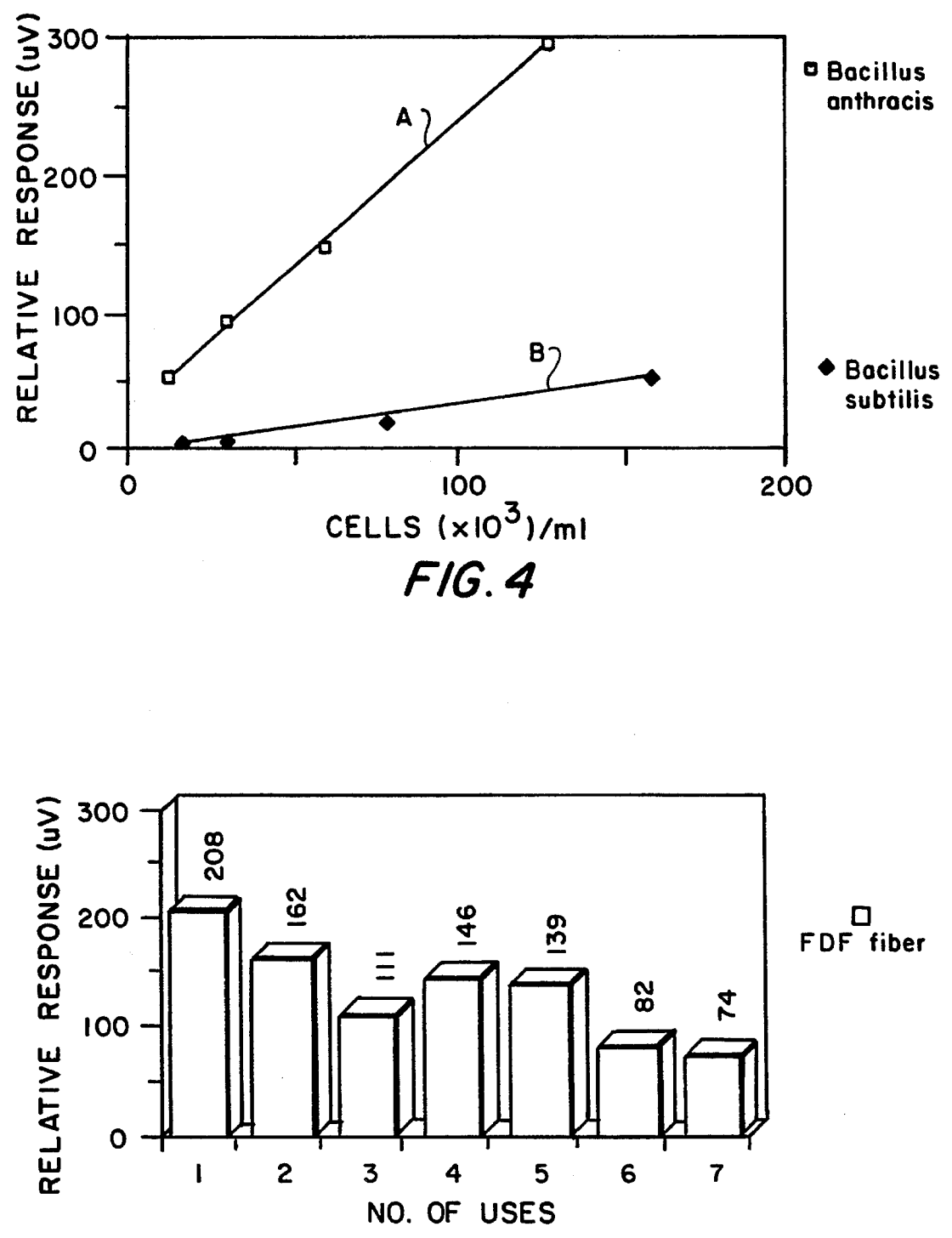

Reusability of the assay apparatus was tested as follows: A fiber coated with the specific antibody FDF-1B9 was exposed to Nile red-stained *B. anthracis* (vegetative cells) at a concentration of 400 cells/µl to measure the fluorescence signal. The cells were removed from the antibody-coated fiber after each measurement by washing with tetraethylamine, 0.05M, pH 11.8, for about 15 minutes before reexposure to same cell solution. In this way, response of the sensor at 400 cells/µl was recorded 7 times (i.e. no. of uses) as shown in FIG. 5.

No effort was made to optimize the conditions for releasing the cells from the antibody. Acid solutions, as well as basic solutions, have been found to be effective in dissociating antigen-antibody complexes. As the removal conditions were not optimized for this antibody, no effort was made to determine the maximum number of times that the assay system could be reused. Thus, while this assay does demonstrate reusability, the number 7 is not significant.

EXAMPLE 7

Demonstration of Assay Performance in Environmental and Clinical Samples

Figure 6:
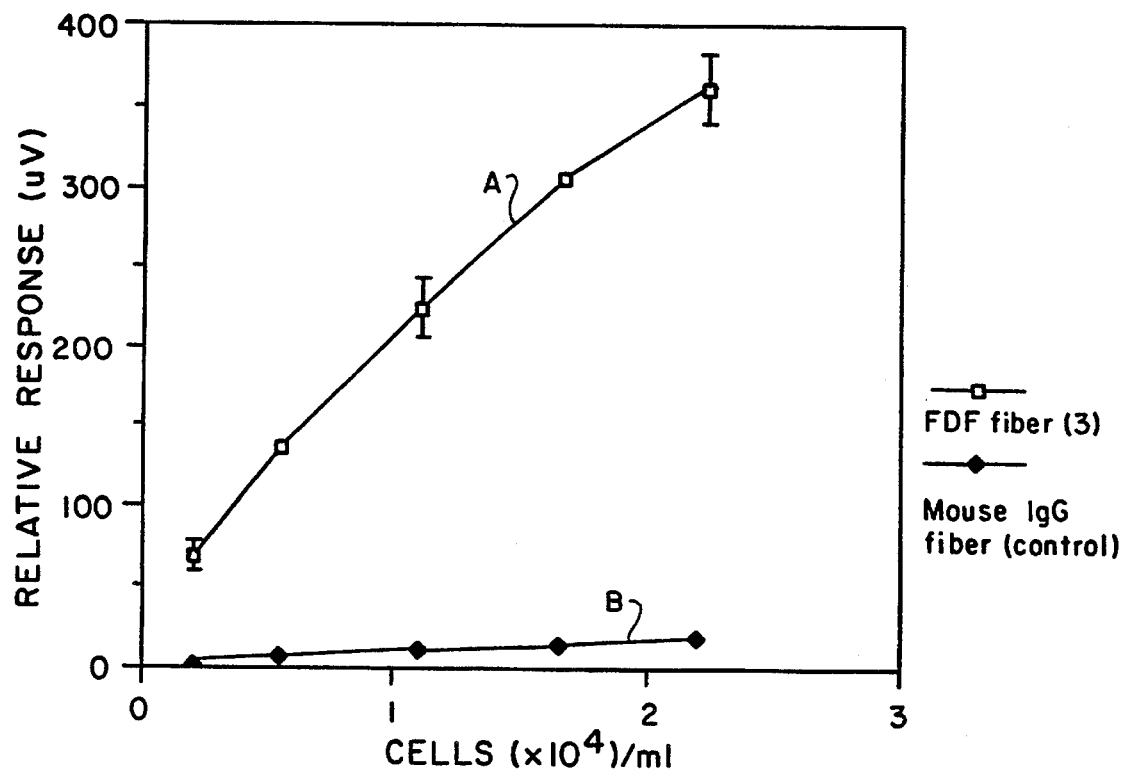
Figure 7:
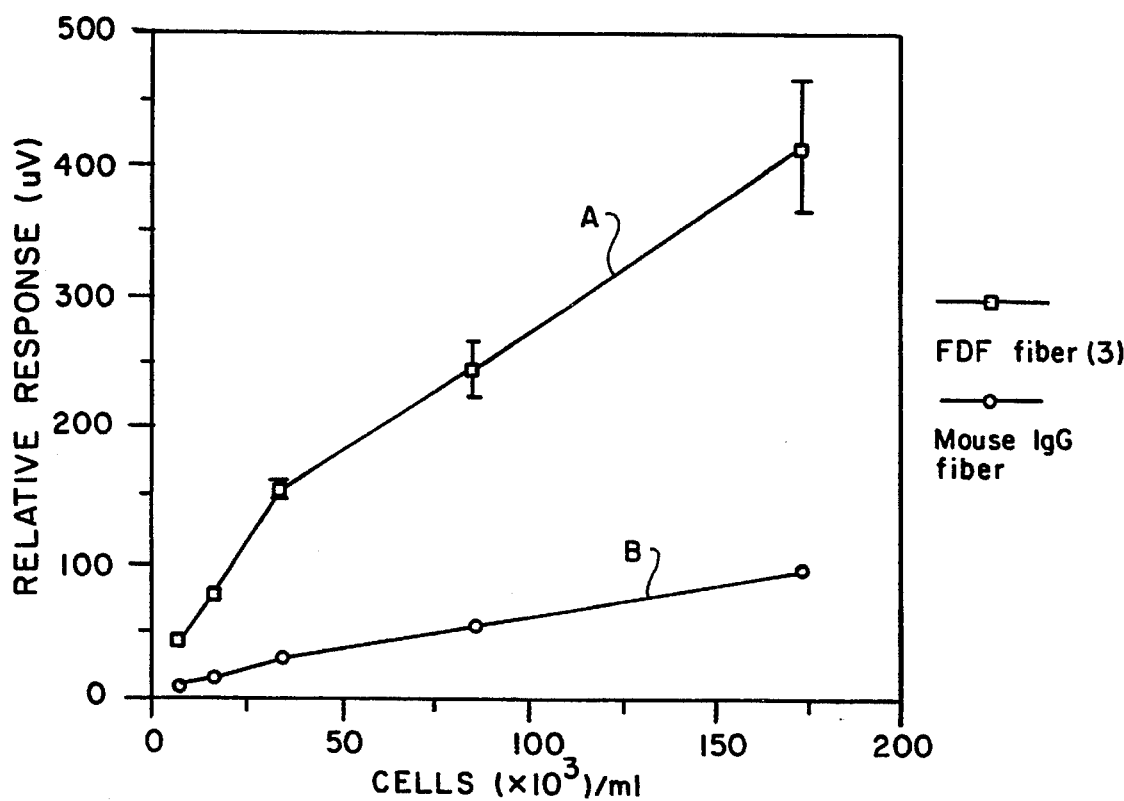

*B. anthracis* cells were introduced into serum or river water at various concentrations. The assay was performed as described in EXAMPLE 2. Results in FIG. 6 and FIG. 7 indicate that the fluorescence responses were proportional to the concentration of the bacteria and that less than 5000 cells/ml were detectable in river water and serum, respectively. In FIG. 6, curve A was produced by a complex of Nile red, *B. anthracis* and FDF-1B9. Curve B was produced by a complex of Nile red and *B. anthracis* in the presence of an optical fiber coated with mouse immunoglobulin G (mouse IgG). In FIG. 7, curve A was produced by a complex of Nile red, *B. anthracis* and FDF-1B9. Curve B was produced by a complex of Nile red and *B. anthracis* in the presence of an optical fiber coated with mouse immunoglobulin G (mouse IgG).

EXAMPLE 8

Detection of Ethidium Bromide-Stained Salmonella Cell Fragments Using Microscopy Salmonella and an antibody specific for its flagella were provided by Dr. Eleanor Metcalf, Uniformed Services University of the Health Sciences (Bethesda, Md.). The antibody was immobilized on acid-cleaned microscope slides using the procedure of EXAMPLE 2. The antibody-coated slides were stored in PBS at pH 7.4 until use.

A stock solution of 0.1 mg/ml ethidium bromide in PBS at pH 7.4 buffer was prepared. In an Eppendorf tube, 90 µl of the Salmonella cell sample was mixed with 10 µl of the ethidium bromide solution. The mixture was allowed to incubate for 5 minutes, then the solution was centrifuged in an Eppendorf tube for 1 minute. The supernatant was removed, leaving the cell pellet. The cells were diluted to a known concentration in PBS at pH 7.4 with 2 mg/ml bovine serum albumin (BSA) for exposure to an antibody-coated microscope slide. The stained cell sample was incubated with the antibody-coated microscope slide for 1 hr, then rinsed with PBS at pH 7.4 with rapid shaking. The shaking caused the cells to break apart leaving fragments attached to the immobilized antibodies. Controls were performed with a non-specific immunoglobulin G (IgG). The slides were examined under a fluorescence microscope. Cell fragments were clearly visible on the slide coated with specific antibody but not on the control slides.

EXAMPLE 9

Detection of Ethidium Bromide-Stained Salmonella Cells Using Microscopy

The procedure in EXAMPLE 8 was followed with the following modification. The cell-coated slide was rinsed 3 times in PBS at pH 7.4 gently so as to prevent cell fragmentation. Again, controls were performed with a non-specific immunoglobulin G (IgG) and cells stained with the ethidium bromide. The slips were examined under a fluorescence microscope. Stained, intact cells were visible on slides coated with specific antibody, but not on the control slides.

EXAMPLE 10

Figure 8:
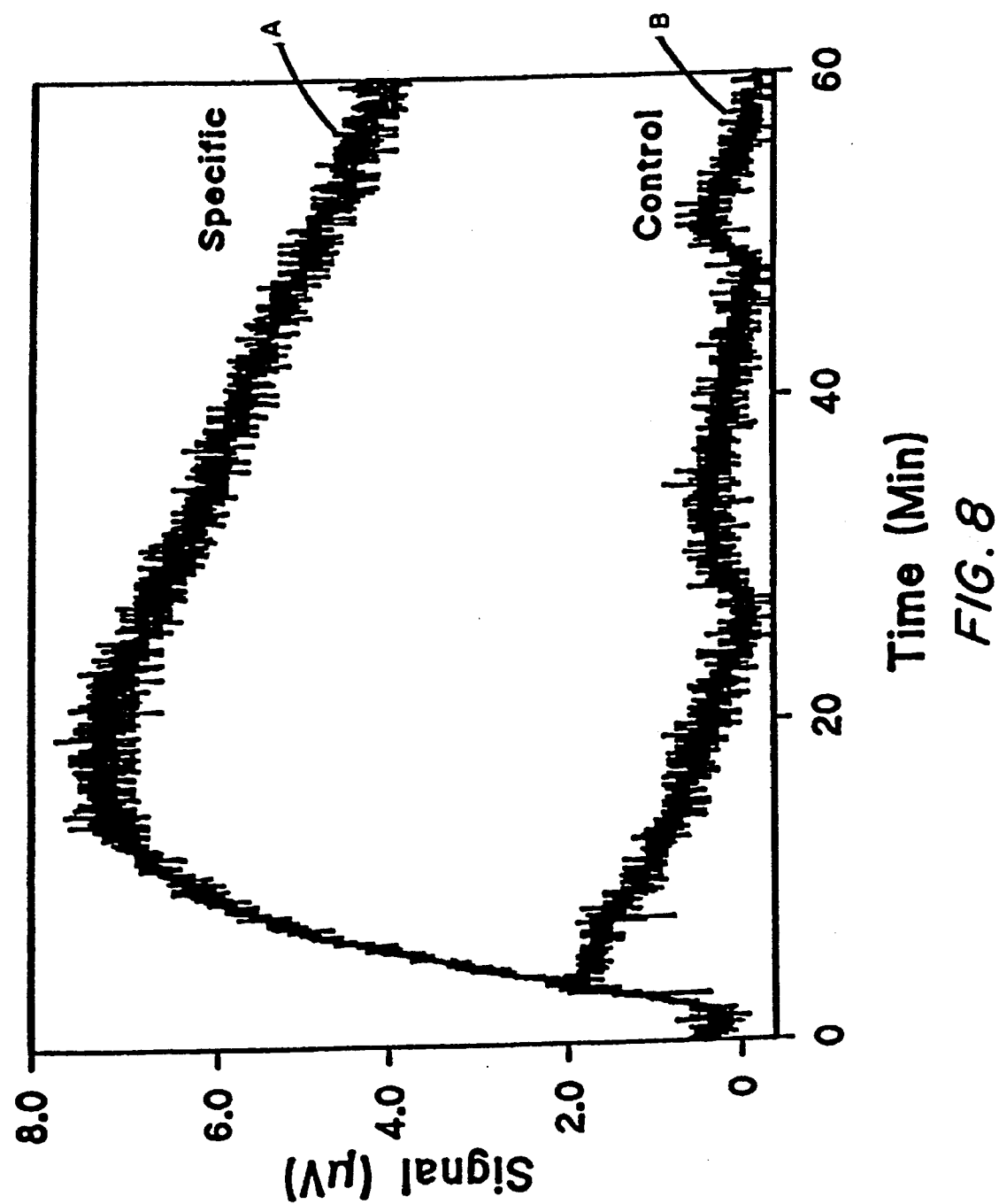

Detection of Ethidium Bromide-Stained Salmonella Cells Using a Fiber Optic Biosensor The procedure of EXAMPLE 8 was followed using stained Salmonella cells except that the antibody was immobilized on an optical fiber as described in EXAMPLE 2, FIG. 2. The antibody-coated fiber, which was attached to a fiber optic fluorimeter (described in EXAMPLE 2), was immersed in a sealed 5 ml pipet that contained PBS and ethidium bromide-stained Salmonella cells ($2.7 \times 10^6$ cells/ml). The fluorescence signal was monitored continuously for at least 60 minutes. No washing steps were performed. FIG. 8 displays the fluorescence signal generated by specific and control fibers. In FIG. 8, curve A is produced by a complex of Nile red, Salmonella and a Salmonella-specific antibody. Curve B is produced by a complex of Nile red and Salmonella in the presence of an optical fiber coated with non-specific immunoglobulin G (IgG).

What is claimed is:

1. A method for detecting the presence of a microbial analyte within a sample suspected of containing said microbial analyte comprising the steps of:

(a) adding a dye in a concentration sufficient to stain biological elements in said sample thereby forming a stained sample;

(b) binding a capture molecule, specific for said microbial analyte, to an optical waveguide;

(c) exposing said stained sample to said capture molecule bound to said optical waveguide, whereby, if said stained sample contains said microbial analyte, then a complex of said dye, said microbial analyte and said capture molecule forms; and (d) optically measuring the formation of said complex by an evanescent wave measurement.

2. The method of claim 1 wherein said dye is a nonspecific dye.

3. The method of claim 1 wherein said capture molecule is an antibody,

4. The method of claim 1 wherein said evanescent wave measurement of said optically measuring step further comprises:
   (a) exciting said complex; and
   (b) detecting a fluorescence signal.

5. The method of claim 1 wherein said evanescent wave measurement of said optically measuring step further comprises:
   (a) exciting said complex; and
   (b) detecting a luminescence signal.

* * * * *